United States Patent
Kondo et al.

(10) Patent No.: US 7,579,297 B2
(45) Date of Patent: Aug. 25, 2009

(54) METHOD FOR PRODUCING CATALYST FOR PRODUCTION OF UNSATURATED ALDEHYDE AND UNSATURATED CARBOXYLIC ACID

(75) Inventors: Masahide Kondo, Hiroshima (JP); Hiroyuki Naitou, Hiroshima (JP); Toru Kuroda, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/582,859

(22) PCT Filed: Dec. 9, 2004

(86) PCT No.: PCT/JP2004/018402

§ 371 (c)(1),
(2), (4) Date: Jun. 14, 2006

(87) PCT Pub. No.: WO2005/058497

PCT Pub. Date: Jun. 30, 2005

(65) Prior Publication Data

US 2007/0149809 A1    Jun. 28, 2007

(30) Foreign Application Priority Data

Dec. 18, 2003   (JP) .............................. 2003-421279

(51) Int. Cl.
| | |
|---|---|
| *B01J 23/18* | (2006.01) |
| *B01J 23/28* | (2006.01) |
| *B01J 23/31* | (2006.01) |
| *B01J 23/843* | (2006.01) |
| *B01J 23/881* | (2006.01) |
| *B01J 23/887* | (2006.01) |
| *B01J 21/06* | (2006.01) |
| *C07C 51/235* | (2006.01) |
| *C07C 51/16* | (2006.01) |
| *C07C 45/27* | (2006.01) |

(52) U.S. Cl. ........................ 502/311; 502/255; 560/211; 562/534; 562/535; 562/546; 562/547; 568/400; 568/449; 568/491

(58) Field of Classification Search ................. 568/491, 568/400, 449; 560/211; 562/534, 546, 547, 562/535; 502/255, 311
See application file for complete search history.

(56) References Cited

U.S. PATENT DOCUMENTS

| | | |
|---|---|---|
| 2004/0267048 A1 | 12/2004 | Kondo et al. |
| 2005/0159619 A1 | 7/2005 | Kondo et al. |
| 2007/0149809 A1 | 6/2007 | Kondo et al. |

FOREIGN PATENT DOCUMENTS

| | | | |
|---|---|---|---|
| JP | 03-109946 | 5/1991 | |
| JP | 04-004048 | 1/1992 | |
| JP | 07-016464 | 1/1995 | |
| JP | 10-028877 | 2/1998 | |
| JP | 2002-282695 | 10/2002 | |
| WO | WO 02076611 | * 10/2002 | |

OTHER PUBLICATIONS

U.S. Appl. No. 10/582,859, filed Jun. 14, 2006, Kondo, et al.
U.S. Appl. No. 11/994,654, filed Jan. 4, 2008, Kondo, et al.

* cited by examiner

*Primary Examiner*—Wayne Langel
*Assistant Examiner*—Brittany M Martinez
(74) *Attorney, Agent, or Firm*—Oblon, Spivak, McClelland, Maier & Neustadt, P.C.

(57) ABSTRACT

A method for producing a catalyst containing at least molybdenum, bismuth and iron including the steps of kneading particles containing catalyst components, an organic binder and a liquid, where the organic binder contains at least a high-viscosity organic binder having a viscosity of from 5,000 mPa·s to 25,000 mPa·s and a low-viscosity organic binder having a viscosity of from 10 mPa·s to less than 5,000 mPa·s, and extrusion molding the resultant kneaded mixture is provided.

3 Claims, No Drawings

METHOD FOR PRODUCING CATALYST FOR PRODUCTION OF UNSATURATED ALDEHYDE AND UNSATURATED CARBOXYLIC ACID

CROSS-REFERENCE TO RELATED APPLICATIONS

The present application claims priority from Japanese patent application 2003-421279, filed Dec. 18, 2003, and PCT patent application PCT/JP04/18402, filed Dec. 9, 2004, the contents of which are incorporated by reference herein.

FIELD OF THE INVENTION

The present invention relates to a catalyst containing at least molybdenum, bismuth and iron for use in producing an unsaturated aldehyde and an unsaturated carboxylic acid through gas-phase catalytic oxidation of propylene, isobutylene, tertiary butyl alcohol (in some cases expressed as TBA) or methyl tertiary butyl ether (in some cases expressed as MTBE) with molecular oxygen, a method for producing a catalyst for use in producing an unsaturated aldehyde and an unsaturated carboxylic acid, and a method for producing an unsaturated aldehyde and an unsaturated carboxylic acid.

DISCUSSION OF THE BACKGROUND

So far, there have been many proposals concerning catalysts for use in producing unsaturated aldehydes and unsaturated carboxylic acids through gas-phase catalytic oxidation of propylene, isobutylene, TBA or MTBE and methods for producing such catalysts.

Most of such catalysts have a composition containing at least molybdenum, bismuth and iron and molded catalysts having such a composition are industrially used. These catalysts are classified into an extrusion-molded catalyst, a supported catalyst or the like depending on their methods of molding. Normally, the extrusion-molded catalyst is produced through the steps of kneading particles containing catalyst components and molding the resultant kneaded mixture.

In Patent document 1, a method of adding a certain cellulose derivative when a catalyst is extrusion-molded is disclosed. Further, in Patent document 1, it is disclosed that a cellulose derivative having a viscosity of its 2% water solution in the range of 1,000 to 10,000 cps at 20° C. is used, and when the viscosity exceeds 10,000 cps, an extrusion moldability of the material to which the cellulose derivative has been added becomes deteriorated and there is little effect on the improvement of the moldability.

Further, in Patent document 2, a method for producing an extrusion-molded catalyst is disclosed, wherein two kinds of binder, namely, hydroxypropyl methylcellulose and curdlan are used, and it is further disclosed that as a cellulose derivative which can be used as a molding aid, one having a viscosity of its 2% water solution in the range of 1,000 to 10,000 mPa·s at 20° C. is preferable because of the good moldability.

However, catalysts obtained by these publicly known methods are not always sufficient as an industrial catalyst in respect of catalyst activity, selectivity to a target product and the like and hence a further improvement has been generally desired from the industrial point of view.

Patent document 1: Japanese Patent Application, First Publication No. Hei 7-16,464

Patent document 2: Japanese Patent Application, First Publication No. 2002-282,695

SUMMARY OF THE INVENTION

The objects of the present invention are to provide a catalyst for use in producing an unsaturated aldehyde and an unsaturated carboxylic acid, which is excellent in catalyst activity and selectivity to the unsaturated aldehyde and the unsaturated carboxylic acid, a method for producing the catalyst and a method for producing an unsaturated aldehyde and an unsaturated carboxylic acid in a high activity and a high selectivity by using the catalyst.

To achieve the objects described above, the present inventors have intensively researched viscosity, a method of addition, amount of addition and the like of an organic binder to be added at the time of extrusion molding, and have surprisingly found that by using two or more kinds of specified organic binders, each of which is different in its viscosity, it is possible to produce a catalyst which is excellent in catalyst activity and selectivity.

The present invention relates to a method for producing a catalyst containing at least molybdenum, bismuth and iron for use in producing an unsaturated aldehyde and an unsaturated carboxylic acid through gas-phase catalytic oxidation of propylene, isobutylene, TBA or MTBE with molecular oxygen, comprising the steps of:

kneading particles containing catalyst components, an organic binder and a liquid; and extrusion molding the resultant kneaded mixture, wherein the organic binder contains at least a high-viscosity organic binder having a viscosity (of its 1% water solution or dispersion at 20° C.) of from 5,000 mPa·s to 25,000 mPa·s and a low-viscosity organic binder having a viscosity (of its 1% water solution or dispersion at 20° C.) of from 10 mPa·s to less than 5,000 mPa·s.

The present invention further relates to a catalyst for use in producing an unsaturated aldehyde and an unsaturated carboxylic acid produced by the above-mentioned method for producing the catalyst.

The present invention also relates to a method for producing an unsaturated aldehyde and an unsaturated carboxylic acid through gas-phase catalytic oxidation of propylene, isobutylene, TBA or MTBE with molecular oxygen by using the above-mentioned catalyst of the present invention.

The catalyst for use in producing an unsaturated aldehyde and an unsaturated carboxylic acid of the present invention is excellent in catalyst activity and selectivity to the unsaturated aldehyde and the unsaturated carboxylic acid, and by using this catalyst, it is possible to produce the unsaturated aldehyde and the unsaturated carboxylic acid in high yield.

DETAILED DESCRIPTION OF THE INVENTION

The catalyst of the present invention is used in producing an unsaturated aldehyde and an unsaturated carboxylic acid through gas-phase catalytic oxidation of propylene, isobutylene, TBA or MTBE, or mixtures thereof, which serves as a raw material of the reaction, with molecular oxygen.

The unsaturated aldehyde and the unsaturated carboxylic acid mentioned above relates to the raw material used, for example, acrolein and acrylic acid are the compounds of interest where the raw material of the reaction is propylene, and methacrolein and methacrylic acid in the case that the raw material of the reaction is a raw material other than propylene.

The catalyst of the present invention is an extrusion-molded catalyst containing at least molybdenum, bismuth and iron as catalyst components. The catalyst components may include, other than these components, silicon, cobalt, nickel, chromium, lead, manganese, calcium, magnesium, niobium, silver, barium, tin, tantalum, zinc, phosphorus, boron, sulfur, selenium, tellurium, cerium, tungsten, antimony, titanium, lithium, sodium, potassium, rubidium, cesium, thallium and the like.

The extrusion-molded catalyst containing at least molybdenum, bismuth and iron as mentioned above is generally produced through the steps of (1) producing particles containing catalyst components, (2) kneading the resultant particles containing catalyst components and the like, (3) extrusion molding the resultant kneaded mixture, and (4) drying and/or heat treating the resultant extrusion-molded article.

In the present invention, the step (1) is not particularly limited and conventionally known methods can be used. Preferably, an aqueous slurry containing at least molybdenum, bismuth and iron is dried and further pulverized to particles.

The method for producing the aqueous slurry containing at least molybdenum, bismuth and iron is not particularly limited and a conventionally well-known precipitation method, oxide mixing method or the like can be used to produce the aqueous slurry, provided that the methods used do not cause undesirable maldistribution of the components.

As the raw materials of the catalyst components to be dissolved in the aqueous slurry, oxides, sulfates, nitrates, carbonates, hydroxides, ammonium salts, halides or the like of each element, or mixtures thereof, can be used. For example, as a raw material of molybdenum, ammonium paramolybdate and molybdenum trioxide can be used.

The method for drying the aqueous slurry to obtain particles is not particularly limited and, for example, a drying method using spray dryer, a drying method using slurry dryer, a drying method using drum dryer or a drying method using evaporation followed by pulverizing the resultant dried block material can be used. Among these methods, the drying method using spray dryer to obtain dried spherical particles is preferable because the particles can be obtained at the same time of drying and the resultant dried particles have a regular spherical shape. Drying conditions differ depending on the drying method used. For example, in the case of using spray dryer, the inlet temperature is normally 100 to 500° C. and the outlet temperature is normally 100° C. or more, preferably 105 to 200° C.

In some cases, the dried particles thus obtained contain salts such as nitrates originating from the raw materials of the catalysts, and the strength of the molded articles may be lowered when these salts are decomposed by calcinations after the molding of the particles. Consequently, it is preferable not only to dry the particles but also to calcine them and make them as calcined particles at this point. The calcining condition used is not particularly limited, and publicly known calcining conditions can be used. Normally, calcination is carried out in the presence of oxygen, air, nitrogen, nitrogen oxides or the like and in the temperature range of 200 to 600° C., and the calcining time is properly chosen in accordance with a target catalyst.

When average particle diameter of the particles containing catalyst components becomes large, large voids are formed at the interstices of the particles, in other words, large pores are formed so that selectivity has a tendency to improve. On the other hand, when the average particle diameter becomes small, the number of contact points among the particles per unit volume increases so that the mechanical strength of the resultant molded catalyst has a tendency to improve. In view of these, the average particle diameter is preferably 10 to 150 µm, more preferably 20 to 100 µm.

Then, in the step (2), the particles obtained in the step (1), a liquid and an organic binder are kneaded. The apparatus to be used in kneading is not particularly limited and, for example, a batch type kneader equipped with dual arm type mixing blade, a continuous kneader such as axial rotation reciprocating screw type or self-cleaning type can be used, however, the batch type is preferable, because kneading can be carried out while checking the state of the kneaded material. Further, the end point of kneading can be determined by visual observation or feel. The mixing method of the aforementioned particles, the liquid and the organic binder is not particularly limited. Specifically, a method in which the particles are dry mixed with the organic binder first, and then the resultant mixture is mixed with the liquid, a method in which the organic binder is dissolved or dispersed in the liquid first, and then the resultant mixture is mixed with the particles or the like can be used. Preferably, the particles are dry mixed with the organic binder first, and then the resultant mixture is mixed with the liquid.

As the liquid to be used in the step (2), water or alcohol is preferable, and as examples of the alcohol, lower alcohol such as ethyl alcohol, methyl alcohol, propyl alcohol or butyl alcohol can be used. Among these liquids, water is especially preferable from the viewpoint of cost and easiness of handling. These liquids can be used alone or in combination with each other.

The amount of the liquid to be used is properly selected depending on the kind or size of the particles, the kind of the liquid or the like. However, it is normally 10 to 60 parts by mass, preferably 20 to 50 parts by mass per 100 parts by mass, of the dried or calcined particles obtained in the step (1).

In the step (2), an organic binder containing at least two kinds of organic binders, each of which having a different viscosity, can be used. In the present invention, an organic binder having the highest viscosity among organic binders contained in the organic binder is expressed as high-viscosity organic binder and an organic binder having the lowest viscosity is expressed as low-viscosity organic binder. The viscosity of the high-viscosity organic binder or the low-viscosity organic binder means a viscosity measured with a 1% by mass solution or dispersion of each organic binder at 20° C. and can be measured, for example, with a viscometer such as model B viscometer. The viscosity of the binder should be measured with solution as long as possible and measurement with dispersion should be limited only in the case that the binder does not dissolve under the aforementioned conditions of concentration and temperature, when the viscosity of the dispersions should be measured under the condition that the liquid phase thereof is in the state of saturated solution. Further, in the case where the organic binder is a polymer compound, the viscosity of it is sometimes different even among the products having the same name because of the difference in the molecular weight and the like.

The high-viscosity organic binder to be used in the present invention has a viscosity of from 5,000 mPa·s to 25,000 mPa·s. The high-viscosity organic binder preferably has a viscosity of from 10,000 mPa·s to 20,000 mPa·s. Further, the low-viscosity organic binder to be used in the present invention has a viscosity of from 10 mPa·s to less than 5,000. The low-viscosity organic binder preferably has a viscosity of from 10 mPa·s to 500 mPa·s, more preferably from 20 mPa·s to 350 mPa·s.

When the high-viscosity organic binder having the viscosity of from 5,000 mPa·s to 25,000 mPa·s and the low-viscosity organic binder having the viscosity of from 10 mPa·s to less than 5,000 mPa·s are used in the form of mixture, the activity and selectivity of the catalyst are improved.

The reason is not clear why moldability and catalyst performance such as activity and selectivity are improved by using the high-viscosity organic binder which, to date, has not been used so far in catalyst systems such as those in the present invention because of deteriorated moldability when in the form of mixture with the low-viscosity organic binder. But, although not bound by this theory, it is supposed, as for the improvement of the moldability, that molding pressure is partially lowered by the homogeneous existence of the kneaded material of the low-viscosity organic binder, even in a small amount, within the kneaded material of the high-viscosity organic binder to improve the moldability. Further, it is supposed, as for the improvement of the catalyst performance, that preferable pores for the catalytic reaction are formed during the drying step, owing to a slight difference in shrinking behavior of each of the high viscosity and the low viscosity portion at the time of drying after molding, to improve the activity and selectivity of the catalyst.

Moreover, when the high-viscosity organic binder is used, even in a small amount, a molded article with high strength can be obtained so that the amount of the organic binder to be used can be reduced and heat treatment for the removal of the binder after drying is accordingly simplified. Consequently, the problem of the lowering of the catalyst performance caused by the reduction of the catalyst at the time of the heat treatment is considerably improved.

The kind of the organic binder is not particularly limited. For example, a cellulose derivative such as methyl cellulose, ethyl cellulose, carboxymethyl cellulose, sodium carboxymethyl cellulose, hydroxyethyl cellulose, hydroxypropyl cellulose, hydroxypropylmethyl cellulose, hydroxyethylmethyl cellulose, hydroxybutylmethyl cellulose or ethylhydroxyethyl cellulose, or a water soluble or water dispersible synthetic polymer compound such as polyvinyl alcohol, or a β-1,3-glucan such as curdlan, laminaran, paramylon, callose, pachyman or scleroglucan can be used.

As the high-viscosity organic binder, methyl cellulose, hydroxypropylmethyl cellulose and hydroxyethylmethyl cellulose are especially preferable. The proportion of the high-viscosity organic binder to the total organic binder is preferably 95 to 50% by mass, more preferably 85 to 65% by mass. Preferably, the amount of the high-viscosity organic binder to be used is from 95 to 50% by mass because strength of the molded article is greatly improved.

As the low-viscosity organic binder, methyl cellulose, hydroxypropylmethyl cellulose, hydroxyethylmethyl cellulose, curdlan and paramylon are especially preferable. The proportion of the low-viscosity organic binder to the total organic binder is preferably 5 to 50% by mass, more preferably 10 to 35% by mass. Preferably, the amount of the low-viscosity organic binder to be used is from 5 to 50% by mass because moldability is considerably improved.

Further, it has been found in the present invention that temperature of the liquid to be added or rate of adding the liquid at the time of kneading exerts influence on moldability. The temperature of the liquid is preferably 20° C. or less, more preferably 10° C. or less. The rate of adding the liquid is preferably 0.3 part by mass/min. or less, more preferably 0.2 part by mass/min. per 1 part by mass of the particles containing catalyst components.

The organic binder may be used either in a purified state or without purification, however, it is preferable to keep the amount of impurities such as metals and residue on ignition as small as possible because these impurities sometimes cause deterioration of the catalyst performance.

The amount of the organic binder to be used is properly selected depending on the kind or size of the particles, the kind of the liquid or the like, however, it is normally 0.05 to 15 parts by mass, preferably 0.1 to 10 parts by mass per 100 parts by mass of the particles obtained in the step (1). Moldability tends to be improved as the amount of the organic binder to be added increases and post-treatment such as heat treatment after molding tends to be simplified as the amount of the organic binder to be added decreases.

Further, in the present invention, inert carrier such as conventionally known inorganic compounds which include silica, alumina, silica-alumina, silicon carbide, titania, magnesia, graphite, diatomite, glass fiber, ceramic ball, stainless steel or inorganic fiber such as ceramic fiber or carbon fiber can be added. Addition may be performed at the time of kneading in the step (2).

Then, in the step (3), the kneaded material obtained in the step (2) is extrusion molded. When the kneaded material of the particles containing catalyst components, the organic binder and the liquid are extrusion molded, auger type extruder, piston type extruder or the like can be used.

The shape of the molded article made by extrusion molding is not particularly limited and ring shape, cylindrical shape, starlike shape or the like can be optionally chosen.

Then, in the step (4), the molded article of the catalyst obtained in the step (3) is dried and calcined to obtain a catalyst (product).

The method of drying is not particularly limited and a publicly known method such as hot air drying, wet drying, far infrared drying, microwave drying or the like can be optionally used. The drying conditions can be properly selected based on a target moisture content.

The dried molded article is normally calcined. However, in the case that the particles have been calcined in the step (1), the step of calcination can be omitted. The calcining conditions are not particularly limited and a publicly known calcining condition can be applied. Normally, calcination is carried out in the temperature range of 200 to 600° C.

The catalyst containing at least molybdenum, bismuth and iron produced by the methods of the present invention preferably has a composition represented by the following general formula (1).

$$Mo_aBi_bFe_cM_dX_eY_fZ_gSi_hO_i \qquad (1)$$

wherein Mo, Bi, Fe, Si and O represent molybdenum, Bismuth, iron, silicon and oxygen, respectively; M represents at least one element selected from the group consisting of cobalt and nickel; X represents at least one element selected from the group consisting of chromium, lead, manganese, calcium, magnesium, niobium, silver, barium, tin, tantalum, and zinc; Y represents at least one element selected from the group consisting of phosphorus, boron, sulfur, selenium, tellurium, cerium, tungsten, antimony and titanium; Z represents at least one element selected from the group consisting of lithium, sodium, potassium, rubidium, cesium and thallium; and subscripts a, b, c, d, e, f, g h and i represent an atomic ratio of each element, respectively; when a is 12, b is in the range of from 0.01 to 3, c is in the range of from 0.01 to 5, d is in the range of from 1 to 12, e is in the range of from 0 to 8, f is in the range of from 0 to 5, g is in the range of from 0.001 to 2 and h is in the range of from 0 to 20 and i represents the atomic ratio of oxygen necessary for fulfilling the requirement of the valence of each element mentioned above.

In the method for producing an unsaturated aldehyde and an unsaturated carboxylic acid of the present invention, propylene, isobutylene, TBA or MTBE which is a raw material of the reaction is subjected to gas-phase catalytic oxidation with molecular oxygen in the presence of the catalyst produced by the method of the present invention. The reaction is normally carried out in a fixed bed. The catalyst may be packed either in one layer or in two or more layers.

The concentration of propylene, isobutylene, TBA or MTBE which is raw material of the reaction in the feed gas can vary widely. Normally, the concentration of the raw material of the reaction in the feed gas is preferably 1 to 20% by volume.

It is economical to use air as a source of molecular oxygen. However, pure oxygen-enriched air can be used when it is necessary. The molar ratio (volume ratio) of the raw material of the reaction to oxygen in the feed gas is preferably 1:0.5 to 1:3.

The feed gas preferably contains water. The concentration of water in the feed gas is preferably 1 to 45% by volume. Further, it is preferable to use water diluted with inert gas such as nitrogen or carbon dioxide.

The reaction pressure is preferably from normal pressure (atmospheric pressure) to several hundred kilopascals. The reaction temperature can be selected normally in the range of from 200 to 450° C. and preferably from 250 to 400° C. in particular. The contact time is preferably 1.5 to 15 seconds.

EXAMPLES

Hereinafter, the present invention will be entered into details with reference to the examples and comparative examples.

The term "part" in the examples and comparative examples means part by mass and a batch type kneader equipped with dual arm type mixing blade was used in kneading. Further the feed gas and the product gas were analyzed with gas chromatograph. The catalyst composition was determined from the charged amount of the raw materials of the catalyst.

The conversion of propylene, isobutylene, TBA or MTBE in the examples and comparative examples (hereinafter expressed as conversion) and the selectivity to an unsaturated aldehyde and an unsaturated carboxylic acid to be produced were determined by the following formulae.

Conversion (%)=$A/B \times 100$

The selectivity to an unsaturated aldehyde (%)=$C/A \times 100$

The selectivity to an unsaturated carboxylic acid (%)=$D/A \times 100$

In these formulae, A is a number of mol(s) of the reacted propylene, isobutylene, TBA or MTBE, B is a number of mol(s) of the supplied propylene, isobutylene, TBA or MTBE, C is a number of mol(s) of the produced unsaturated aldehyde and D is a number of mol(s) of the produced unsaturated carboxylic acid.

Further, the viscosity of an organic binder was measured with 1% by mass water solution or dispersion of the organic binder at 20° C. by using a model B viscometer. The solution or dispersion of the organic binder was prepared by using hot water method and the like to prevent it from coagulation.

Example 1

To 1,000 parts of pure water, 500 parts of ammonium paramolybdate, 6.2 parts of ammonium paratungstate, 1.4 parts of potassium nitrate, 27.5 parts of antimony trioxide and 49.5 parts of bismuth trioxide were added and stirred under heating (Liquid A). Separately, to 1,000 parts of pure water, 114.4 parts of ferric nitrate, 281.6 parts of cobalt nitrate and 42.1 parts of zinc nitrate were added in this order and dissolved (Liquid B). Liquid B was added to Liquid A to obtain an aqueous slurry and the resultant slurry was dried by using spray dryer to obtain dried spherical particles having an average particle diameter of 60 μm. The resultant dried spherical particles were calcined at 300° C. for 1 hour to obtain a calcined catalyst.

To 500 parts of the resultant calcined catalyst, 15 parts of hydroxypropylmethyl cellulose, the viscosity (of a 1% water solution at 20° C.) of which was 16,000 mPa·s, and 10 parts of hydroxypropylmethyl cellulose, the viscosity (of a 1% water solution at 20° C.) of which was 40 mPa·s, were added and dry mixed. To the resultant mixture, 190 parts of pure water, the temperature of which was 5° C., was mixed at a rate of 25 parts/min. (0.05 part/min. per 1 part of the calcined catalyst) and mixed (kneaded) by kneader to the extent to obtain a clayey material and the resultant material was extrusion molded by an auger type extruder to obtain a molded catalyst having an external diameter of 5 mm, an internal diameter of 2 mm and an average length of 5 mm.

Then, the resultant molded catalyst was dried at 110° C. by using hot air dryer to obtain a dried molded catalyst. Then, the resultant dried molded catalyst was calcined again at 510° C. for 3 hours to obtain a finally calcined molded catalyst.

The elemental composition exclusive of oxygen of the resultant molded catalyst was $Mo_{12}W_{0.1}Bi_{0.9}Fe_{1.2}Sb_{0.8}Co_{4.1}Zn_{0.6}K_{0.06}$.

The molded catalyst was packed in a tubular reactor made of stainless steel and the reaction was carried out by using a feed gas containing 5% by volume of propylene, 12% by volume of oxygen, 10% by volume of water vapor and 73% by volume of nitrogen under the condition of normal pressure, contact time of 3.6 seconds and reaction temperature of 310° C. As the result, conversion of propylene was 99.0%, the selectivity to acrolein was 91.1% and the selectivity to acrylic acid was 6.5%.

Example 2

The preparation of the molded catalyst and the reaction were carried out in the same manner as in Example 1 except that 10 parts of curdlan, the viscosity (of a 1% water solution at 20° C.) of which was 35 mPa·s, was used instead of 10 parts of hydroxypropylmethyl cellulose, the viscosity (of a 1% water solution at 20° C.) of which was 40 mPa·s. As the result, conversion of propylene was 99.0%, the selectivity to acrolein was 91.1% and the selectivity to acrylic acid was 6.6%.

Example 3

The preparation of the molded catalyst and the reaction were carried out in the same manner as in Example 1 except that 15 parts of methyl cellulose, the viscosity (of a 1% water solution at 20° C.) of which was 9,000 mPa·s, was used instead of 15 parts of hydroxypropylmethyl cellulose, the viscosity (of a 1% water solution at 20° C.) of which was 16,000 mPa·s, and 10 parts of curdlan, the viscosity (of a 1% water solution at 20° C.) of which was 60 mPa·s, was used instead of 10 parts of hydroxypropylmethyl cellulose, the viscosity (of a 1% water solution at 20° C.) of which was 40 mPa·s. As the result, conversion of propylene was 98.9%, the selectivity to acrolein was 90.9% and the selectivity to acrylic acid was 6.4%.

Example 4

The preparation of the molded catalyst and the reaction were carried out in the same manner as in Example 1 except that 40 parts of hydroxypropylmethyl cellulose, the viscosity (of a 1% water solution at 20° C.) of which was 16000 mPa·s, was used instead of 15 parts of hydroxypropylmethyl cellulose, the viscosity (of a 1% water solution at 20° C.) of which was 16,000 mPa·s, and 20 parts of curdlan, the viscosity (of a 1% water solution at 20° C.) of which was 40 mPa·s, was used instead of 10 parts of hydroxypropylmethyl cellulose, the viscosity (of a 1% water solution at 20° C.) of which was 40 mPa·s. As the result, conversion of propylene was 98.8%, the selectivity to acrolein was 90.8% and the selectivity to acrylic acid was 6.4%.

Example 5

The preparation of the molded catalyst and the reaction were carried out in the same manner as in Example 2 except that two kinds of organic binder were homogeneously dispersed into 190 parts of hot water and the resultant dispersion was cooled to 5° C. and then added to 500 parts of the calcined catalyst at a rate of 25 parts/min. (0.05 part/min. per 1 part of the calcined catalyst) and kneaded. As the result, conversion of propylene was 98.9%, the selectivity to acrolein was 91.0% and the selectivity to acrylic acid was 6.4%.

Comparative Example 1

The preparation of the molded catalyst and the reaction were carried out in the same manner as in Example 3 except that 25 parts of curdlan, the viscosity (of a 1% water solution at 20° C.) of which was 60 mPa·s, was used instead of 15 parts of methyl cellulose, the viscosity (of a 1% water solution at 20° C.) of which was 9,000 mPa·s, and 10 parts of curdlan, the viscosity (of a 1% water solution at 20° C.) of which was 60 mPa·s. As the result, conversion of propylene was 98.8%, the selectivity to acrolein was 90.3% and the selectivity to acrylic acid was 6.2% were obtained. Further, the strength of the catalyst thus obtained was deteriorated in comparison with that obtained in Example 3.

Comparative Example 2

The preparation of the molded catalyst and the reaction were carried out in the same manner as in Example 3 except that 25 parts of methyl cellulose, the viscosity (of a 1% water solution at 20° C.) of which was 9,000 mPa·s, was used instead of 15 parts of methyl cellulose, the viscosity (of a 1% water solution at 20° C.) of which was 9,000 mPa·s, and 10 parts of curdlan, the viscosity (of a 1% water solution at 20° C.) of which was 60 mPa·s. As the result, conversion of propylene was 98.7%, the selectivity to acrolein was 90.4% and the selectivity to acrylic acid was 6.3%.

Comparative Example 3

The preparation of the molded catalyst and the reaction were carried out in the same manner as in Example 1 except that 25 parts of hydroxypropylmethyl cellulose, the viscosity (of a 1% water solution at 20° C.) of which was 40 mPa·s, was used instead of 15 parts of hydroxypropylmethyl cellulose, the viscosity (of a 1% water solution at 20° C.) of which was 16,000 mPa·s, and 10 parts of hydroxypropylmethyl cellulose, the viscosity (of a 1% water solution at 20° C.) of which was 40 mPa·s. As the result, conversion of propylene was 98.9%, the selectivity to acrolein was 90.3% and the selectivity to acrylic acid was 6.1%. Further, the strength of the catalyst thus obtained was deteriorated in comparison with that obtained in Example 1.

Comparative Example 4

The preparation of the molded catalyst and the reaction were carried out in the same manner as in Example 1 except that 25 parts of hydroxypropylmethyl cellulose, the viscosity (of a 1% water solution at 20° C.) of which was 16,000 mPa·s, was used instead of 15 parts of hydroxypropylmethyl cellulose, the viscosity (of a 1% water solution at 20° C.) of which was 16,000 mPa·s, and 10 parts of hydroxypropylmethyl cellulose, the viscosity (of a 1% water solution at 20° C.) of which was 40 mPa·s. The moldability and the product yield of the catalyst were considerably deteriorated. As the result, conversion of propylene was 98.9%, the selectivity to acrolein was 90.4% and the selectivity to acrylic acid was 6.2%.

Example 6

To 1,000 parts of pure water, 500 parts of ammonium paramolybdate, 6.2 parts of ammonium paratungstate, 23.0 parts of cesium nitrate, 24.0 parts of antimony trioxide and 33.0 parts of bismuth trioxide were added and stirred under heating (Liquid A). Separately, to 1,000 parts of pure water, 209.8 parts of ferric nitrate, 75.5 parts of nickel nitrate, 453.3 parts of cobalt nitrate, 31.3 parts of lead nitrate and 2.8 parts of 85% phosphoric acid were sequentially added in this order and dissolved (Liquid B). Liquid B was added to Liquid A to obtain an aqueous slurry and the resultant slurry was dried by using spray dryer to obtain dried spherical particles having an average particle diameter of 60 μm.

The resultant dried spherical particles were calcined at 300° C. for 1 hour and at 510° C. for 3 hours to obtain a calcined catalyst.

To 500 parts of the resultant calcined catalyst, 20 parts of hydroxypropylmethyl cellulose, the viscosity (of a 1% water solution at 20° C.) of which was 15,000 mPa·s, and 5 parts of curdlan, the viscosity (of a 1% water solution at 20° C.) of which was 40 mPa·s, were added and dry mixed. To the resultant mixture, 190 parts of pure water, the temperature of which was 5° C., was mixed at a rate of 25 parts/min. (0.05 part/min. per 1 part of the calcined catalyst) and mixed (kneaded) by kneader to the extent to obtain a clayey material and the resultant material was extrusion molded by an piston type extruder to obtain a molded catalyst having an external diameter of 5 mm, an internal diameter of 2 mm and an average length of 5 mm.

Then, the resultant molded catalyst was dried at 110° C. by using hot air dryer to obtain a dried molded catalyst. Then, the resultant dried molded catalyst was calcined again at 400° C. for 3 hours to obtain a finally calcined molded catalyst.

The elemental composition exclusive of oxygen of the resultant molded catalyst was $Mo_{12}W_{0.1}Bi_{0.6}Fe_{2.2}Sb_{0.7}Ni_{1.1}Co_{6.6}Pb_{0.4}P_{0.1}Cs_{0.5}$.

The molded catalyst was packed in a tubular reactor made of stainless steel and the reaction was carried out by using a feed gas containing 5% by volume of isobutylene, 12% by volume of oxygen, 10% by volume of water vapor and 73% by volume of nitrogen under the condition of normal pressure, contact time of 3.6 seconds and reaction temperature of 340° C. As the result, conversion of isobutylene was 98.0%, the selectivity to methacrolein was 89.9% and the selectivity to methacrylic acid was 4.0%.

Example 7

The preparation of the molded catalyst and the reaction were carried out in the same manner as in Example 6 except that pure water was added at a rate of 175 parts/min. (0.35 part/min. per 1 part of the calcined catalyst). The moldability and the product yield of the catalyst were slightly deteriorated in comparison with those in Example 6. As the result, conversion of isobutylene was 97.9%, the selectivity to methacrolein was 89.9% and the selectivity to methacrylic acid was 3.9%.

Example 8

The preparation of the molded catalyst and the reaction were carried out in the same manner as in Example 6 except that the temperature of pure water was 26° C. The moldability and the product yield of the catalyst were slightly deteriorated in comparison with those in Example 6. As the result, conversion of isobutylene was 97.8%, the selectivity to methacrolein was 89.8% and the selectivity to methacrylic acid was 3.9%.

Comparative Example 5

The preparation of the molded catalyst and the reaction were carried out in the same manner as in Example 6 except that 25 parts of curdlan, the viscosity (of a 1% water solution at 20° C.) of which was 40 mPa·s, was used instead of 20 parts of hydroxypropylmethyl cellulose, the viscosity (of a 1% water solution at 20° C.) of which was 15,000 mPa·s, and 5 parts of curdlan, the viscosity (of a 1% water solution at 20° C.) of which was 40 mPa·s. As the result, conversion of isobutylene was 97.5%, the selectivity to methacrolein was 89.5% and the selectivity to methacrylic acid was 3.5%. Further, the strength of the catalyst thus obtained was deteriorated in comparison with that obtained in Example 6.

Comparative Example 6

The preparation of the molded catalyst and the reaction were carried out in the same manner as in Example 6 except that 25 parts of hydroxypropylmethyl cellulose, the viscosity (of a 1% water solution at 20° C.) of which was 15,000 mPa·s, was used instead of 20 parts of hydroxypropylmethyl cellulose, the viscosity (of a 1% water solution at 20° C.) of which was 15,000 mPa·s and 5 parts of curdlan, the viscosity (of a 1% dispersion at 20° C.) of which was 40 mPa·s. As the result, conversion of isobutylene was 97.6%, the selectivity to methacrolein was 89.6% and the selectivity to methacrylic acid was 3.5%.

Comparative Example 7

The preparation of the molded catalyst and the reaction were carried out in the same manner as in Example 6 except that 20 parts of hydroxypropylmethyl cellulose, the viscosity (of a 1% water solution at 20° C.) of which was 1,600 mPa·s, was used instead of 20 parts of hydroxypropylmethyl cellulose, the viscosity (of a 1% water solution at 20° C.) of which was 15,000 mPa·s. As the result, conversion of isobutylene was 97.6%, the selectivity to methacrolein was 89.7% and the selectivity to methacrylic acid was 3.5%. Further, the strength of the catalyst thus obtained was deteriorated in comparison with that obtained in Example 6.

By the method for producing a catalyst of the present invention, a catalyst excellent in catalyst activity and selectivity to an unsaturated aldehyde and an unsaturated carboxylic acid can be produced and by the use of the catalyst of the present invention, the unsaturated aldehyde and the unsaturated carboxylic acid can be produced in a high yield.

What is claimed is:

1. A method for producing a catalyst comprising at least molybdenum, bismuth and iron for use in producing an unsaturated aldehyde and an unsaturated carboxylic acid through gas-phase catalytic oxidation of propylene, isobutylene, tertiary butyl alcohol or methyl tertiary butyl ether with molecular oxygen, comprising the steps of:

kneading particles comprising catalyst components, an organic binder and a liquid to form a kneaded mixture; and extrusion molding the kneaded mixture, wherein the organic binder comprises at least a high-viscosity organic binder having a viscosity of from 5,000 mPa·s to 25,000 mPa·s and a low-viscosity organic binder having a viscosity of from 10 mPa·s to less than 5,000 mPa·s, wherein viscosity is measured with a 1% by mass water solution or dispersion of the binder at 20° C.

2. The method for producing the catalyst according to claim 1, wherein the liquid is added at the time of kneading at a rate of 0.2 parts by mass/min per 1 part by mass of the particles or less comprising the catalyst components.

3. The method for producing the catalyst according to claim 1, wherein the temperature of the liquid is 20° C. or less.

* * * * *